(12) United States Patent
Pang

(10) Patent No.: US 7,488,723 B2
(45) Date of Patent: Feb. 10, 2009

(54) USE OF NON-FEMINIZING ESTROGENS AS TREATMENT FOR RETINAL VASCULAR DISEASES

(75) Inventor: Iok-Hou Pang, Grand Prairie, TX (US)

(73) Assignee: Alcon, Inc., Hunenberg (CH)

( * ) Notice: Subject to any disclaimer, the term of this patent is extended or adjusted under 35 U.S.C. 154(b) by 962 days.

(21) Appl. No.: 10/226,943

(22) Filed: Aug. 23, 2002

(65) Prior Publication Data

US 2003/0050295 A1 Mar. 13, 2003

Related U.S. Application Data

(60) Provisional application No. 60/317,223, filed on Sep. 5, 2001.

(51) Int. Cl.
*A61K 31/56* (2006.01)
(52) U.S. Cl. ................................................ 514/171
(58) Field of Classification Search .................. 514/171
See application file for complete search history.

(56) References Cited

U.S. PATENT DOCUMENTS

| | | | |
|---|---|---|---|
| 5,504,074 A * | 4/1996 | D'Amato et al. ............ 514/182 |
| 5,521,168 A | 5/1996 | Clark |
| 5,843,934 A | 12/1998 | Simpkins |
| 5,859,001 A | 1/1999 | Simpkins et al. |
| 5,877,169 A | 3/1999 | Simpkins |
| 6,001,368 A | 12/1999 | Jenks |
| 6,197,833 B1 | 3/2001 | Simpkins et al. |
| 2002/0082433 A1 * | 6/2002 | Agoston et al. ............. 552/544 |

OTHER PUBLICATIONS

Green et al. "Nuclear estrogen receptor-independent neuroprotection by estratrienes: A novel interaction with glutathione" Neuroscience vol. 84, No. 1, pp. 7-10, 1998.*
Harris-Yitzhak et al. "Estrogen-replacement therapy: Effects on retrobulbar hemodynamics" American Journal of Ophthamology (2000), 129 (5), pp. 623-628.*
Alkayed et al., "Neuroprotective effects of female gonadal steroids in reproductively senescent female rats", Stroke, vol. 31, pp. 161-168 (2000).
Allred et al., "Soy diets containing varying amount of genistein stimulate growth of estrogen-dependent (MCF-7) tumors in a dose-dependent manner", Cancer Res, vol. 61, pp. 5045-5050 (2001).
Chen et al., "The effects of 17beta-estradiol on ischemia-induced neuronal damage in the gerbil hippocampus", Neuroscience, vol. 87, pp. 817-822 (1998).
Controneo and Lamartiniere, Pharmacologic, but not dietary, genistein supports endometriosis in a rat model, Toxicol Sci, vol. 61, pp. 68-75 (2001).
Culmsee et al., "Neuroprotection by estrogens in a mouse model of focal cerebral ischemia and in cultured neurons: evidence for a receptor-independent antioxidative mechanism", J Cereb Blood Flow Metab, vol. 19, pp. 1263-1269 (1999).
Dubal et al., "Estradiol protects against ischemic injury", J Cereb Blood Flow Metab, vol. 18, pp. 1253-1258 (1998).
Green and Simpkins, "Neuroprotective effects of estrogens: Potential mechanisms of action", Int J Dev Neurosci, vol. 18, pp. 347-358 (2000).
Harris-Yitzhak M. et al., "Estrogen-replacement therapy: Effects on retrobulbar hemodynamics", Am J Ophthalmol, vol. 129, pp. 623-628 (2000).
Hawk et al., "Testosterone increases and estradiol decreases middle cerebral artery occlusion lesion size in male rats", Brain Res, vol. 796, pp. 296-298 (1998).
Hum and Macrae, "Estrogen as a neuroprotectant in stroke", J Cereb Blood Flow Metab, vol. 20, pp. 631-652 (2000).
Kondo et al., "Estrogen alleviates cognitive dysfunction following transient brain ischemia in ovariectomized gerbils", Neurosci Lett, vol. 238, pp. 45-48 (1997).
Maggiolini et al., "Estrogen receptor alpha mediates the proliferative but not the cytotoxic dose-dependent effects of two major phytoestrogens on human breast cancer cells", Mol Pharmacol, vol. 60, pp. 595-602 (2001).
Nonaka et al., "Administration of 17 beta-estradiol attenuates retinal ischemia-reperfusion injury in rats", Invest Ophthalmol Vis Sci vol. 41, pp. 2689-2696 (2000).
Pelligrino et al., "Cerebral vasodialting capacity during forebrain ischemia: effects of chronic estrogen depletion and repletion and the role of neuronal nitric oxide synthase", Neuroreport, vol. 9, pp. 3285-3291 (1998).
Rusa et al., "17 beta-estradiol reduces stroke injury in estrogen-deficient female animals", Stroke, vol. 30, pp. 1665-1670 (1999).
Shi et al., "Effects of 17 beta -estradiol on glucose transporter 1 expression and endothelial cell survival following focal ischemia in the rats", Exp Brain Res, vol. 117, pp. 200-206 (1997).
Simpkins et al., "Estrogens may reduce mortality and ischemic damage caused by middle cerebral artery occlusion in the female rat", J Neurosurg, vol. 87, pp. 724-730 (1997).
Toung et al., "Estrogen-mediated neuroprotection after experimental stroke in male rats", Stroke, vol. 29, pp. 1666-1670 (1998).
Wang et al., "Estrogen provides neuroprotection in transient forebrain ischemia through perfusion-independent mechanisms in rats", Stroke, vol. 30, pp. 630-637 (1999).
Yannuzzi et al., "Risk factors for central retinal vein occlusion", Arch Ophthalmol, vol. 114, pp. 545-554 (1996).
Zhang et al., "Effects of gender and estradiol treatment on focal brain ischemia", Brain Res, vol. 784, pp. 321-324 (1998).

* cited by examiner

*Primary Examiner*—Jennifer M Kim
(74) *Attorney, Agent, or Firm*—Teresa J. Schultz

(57) ABSTRACT

The invention provides pharmaceutical compositions containing non-feminizing estrogen and methods of using these compositions to prevent or ameliorate retinal vascular diseases.

3 Claims, No Drawings

USE OF NON-FEMINIZING ESTROGENS AS TREATMENT FOR RETINAL VASCULAR DISEASES

This application claims priority from U.S. Provisional Application Ser. No. 60/317,223 filed Sep. 5, 2001.

BACKGROUND OF THE INVENTION

1. Field of the Invention

The present invention relates to the field of retinal vascular diseases. More specifically, the invention provides a method of treating retinal vascular diseases using compositions comprising at least one non-feminizing estrogens.

2. Description of the Related Art

Retinal or optic nerve head damage, which can result in the loss of vision, is caused by trauma and various pathological events including ischemia, hypoxia, or edema. Retinal or optic nerve head ischemia or hypoxia results when blood supply is significantly reduced to these tissues. Ischemia is a complex pathological episode involving numerous biochemical events. Retinal vascular diseases include retinal arterial obstructive diseases (which includes central retinal artery obstruction, branch retinal artery obstruction, cilioretinal artery obstruction, ophthalmic artery obstruction, combined central retinal artery and vein obstructions, cotton-wool spots), central retinal vein occlusion, and retinal branch vein occlusion.

Currently, numerous therapeutic modalities have been attempted to improve the vision of patients suffering from retinal vascular diseases. For retinal arterial obstructive diseases, anterior chamber paracentesis or intravenous acetazolamide can be employed in order to decrease intraocular pressure and increase retinal perfusion. Inhalation of oxygen-carbon dioxide mixture has been used to induce retinal vasodilation and increase oxygenation to retinal tissues. Sometimes, a direct infusion of a thrombolytic agent into the ophthalmic artery may help the recovery of vision. For retinal vein occlusions, careful evaluation is warranted, and prompt panretinal or sectoral laser photocoagulation may be needed for eyes that develop neovascularization. Unfortunately, all of these treatment modalities are accompanied with significant side effects, ocular and/or systemic. Thus, a satisfactory treatment regimen for improving vision in eyes with these retinal vascular disease is needed.

SUMMARY OF THE INVENTION

The present invention overcomes these and other drawbacks of the prior art by providing compositions comprising at least one non-feminizing estrogen or its metabolites and methods for their use in the treatment of retinal vascular diseases. In particular, the invention provides methods for treating a retinal vascular disease by administering to a patient in need thereof a therapeutically effective amount of a composition including at least one non-feminizing estrogen compound or an analog thereof. The retinal vascular disease may be any retinal vascular disease, such as retinal arterial obstructive disease, central retinal vein occlusion, and retinal branch vein occlusion. In preferred embodiments, the disease to be treated is a retinal arterial obstructive disease such as central retinal artery obstruction, branch retinal artery obstruction, cilioretinal artery obstruction, ophthalmic artery obstruction, combined central retinal artery and vein obstruction, and cotton-wool spots.

It is contemplated that virtually any non-feminizing estrogen compound will be useful in the methods of the invention. Typically, the non-feminizing estrogen compound for use in the methods of the invention will be polycyclic compounds having a terminal phenolic group, in a structure containing at least a second ring, having a molecular mass of less than 1000 Daltons. As used herein, the phrase "non-feminizing estrogen compound" refers to compounds having very little to no feminizing, or sex-related, activity. Examples of such compounds include, but are not limited to, estratriene-3-ol, 3,17α-estradiol, estrone, estriol, and their analogs. Most preferably, the non-feminizing estrogen compound is estratriene-3-ol.

DETAILED DESCRIPTION PREFERRED EMBODIMENTS

Retinal vascular diseases include retinal arterial obstructive diseases (which includes central retinal artery obstruction, branch retinal artery obstruction, cilioretinal artery obstruction, ophthalmic artery obstruction, combined central retinal artery and vein obstructions, cotton-wool spots), central retinal vein occlusion, and retinal branch vein occlusion. These retinal vascular diseases frequently present themselves as a sudden and painless loss of vision. For central and branch retinal vein occlusions, macular edema and retinal neovascularization may develop.

Estrogens have been demonstrated to be protective against ischemia-induced damage in the brain (Kondo et al. 1997; Shi et al. 1997; Simpkins et al. 1997; Chen et al. 1998; Dubal et al. 1998; Hawk et al. 1998; Pellegrino et al. 1998; Toung et al. 1998; Zhang et al. 1998; Culmsee et al. 1999; Rusa et al. 1999; Wang et al. 1999; Alkayed et al. 2000; Green and Simpkins 2000; Hurn and Macrae 2000). Estrogens are also protective against ischemia-induced damage in the eyes of the rat (Nonaka et al, 2000). Furthermore, estrogens are likely involved in the regulation of blood flow in the eye. For example, in women, risk of central retinal vein occlusion decreased with use of postmenopausal estrogens (Yannuzzi et al. 1996). Estrogen-replacement therapy in postmenopausal women apparently helps reduce vascular resistance distal to the ophthalmic artery to levels matching those of young women (Harris-Yitzhak M. et al. 2000).

Classical estrogens or their metabolites are not practical as therapeutic agents for the treatment of retinal diseases because their feminizing effects are not acceptable to many patients. Non-feminizing estrogen compounds are estrogen-related compounds having substantially no sex-related effect on the subject. Simpkins et al. (U.S. Pat. Nos. 6,197,833; 5,877,169; 5,843,934 all incorporated herein by reference) discuss the use of such compounds for treatment of patients with a number of degenerative conditions or conditions resulting from ischemic damage in the brain. Simpkins et al. do not discuss the use of the compounds for the treatment of eye-related diseases.

Estrogen occurs in at least two isomeric forms, including α estrogen and β estrogen. β estrogens are pleotrophic molecules with many biological activities. Clinical uses include treatment of osteoporosis, symptoms of menopause and fertility control. In comparison to β estrogen, α estrogen is typically believed to be at least 100-1000 times less potent in estrogenic activity. Numerous examples have been reported in the literature that show that the biological effects of β estrogen are not shared by the α isomer. In fact, in the art, α estrogen is typically used as a negative control for β estradiol.

Jenks (U.S. Pat. No. 6,001,368) describes the use of phytoestrogenic isoflavones to inhibit or reduce the risk of macular degeneration. Jenks does not discuss the use of non-feminizing estrogens at all. All of the compounds disclosed in Jenks, though structurally different from the prototypical estrogen steroids, are pharmacologically classified as feminizing estrogens. Jenks mentions compounds such as genistin (or genistein), daidzin, glycitin, and their chemical analogs. These phytoestrogens function as feminizing estrogens. For example, they stimulate the growth of estrogen-dependent tumors (Allred et al, 2001); and they support the development of endometriosis (Cotroneo & Lamartiniere, 2001). Their biological effects are mediated by the estrogen receptor, similar to feminizing estrogens (Maggiolini et al, 2001).

Simpkins et al. (U.S. Pat. No. 5,843,934, herein incorporated by reference) showed the α estrogen has a comparable activity to that of β estrogen for neuroprotection. This activity provides α estrogen with a number of advantages over β estrogen in the treatment of degenerative diseases, trauma and aging related to the central nervous system. These advantages arise in situations which require treatment of males where the development of female traits is to be avoided and the treatment of females where the subject has increased susceptibility to endometrial, breast and cervical cancer.

The present inventors show for the first time that non-feminizing estrogens are useful in the treatment of retinal vascular diseases.

The compositions of the present invention may contain additional pharmaceutically active agents or may be dosed concurrently with other pharmaceutical compositions or surgical procedures. In particular, when treating a mammal for the prevention, treatment or amelioration of conditions resulting from retinal vascular diseases, the compositions of the present invention may contain additional agents or may be used concurrently or sequentially with other agents, compositions, or surgical procedures. Examples include: anterior chamber paracentesis, intravenous acetazolamide, inhalation of oxygen-carbon dioxide mixture, a direct infusion of a thrombolytic agent into the ophthalmic artery, panretinal or sectoral laser photocoagulation, or other appropriate agents and procedures known to those skilled in the art.

Obstruction of retinal vessels causes ischemia in the retina, which in turn can cause permanent damage to the retina tissues. The non-feminizing estrogens compounds of the invention may be used to protect cells from the effects of oxygen-deprivation and glucose-deprivation and consequently from energy deprivation associated with ischemia.

It is contemplated that virtually any non-feminizing estrogen compound will be useful in the methods of the invention. Typically, the non-feminizing estrogen compound for use in the methods of the invention will be polycyclic compounds having a terminal phenolic group, in a structure containing at least a second ring, having a molecular mass of less than 1000 Daltons, and excluding feminizing estrogens. Examples of such compounds include, but are not limited to, estratriene-3-ol, 3,17α-estradiol, estrone, estriol, and their analogs. Most preferably, the non-feminizing estrogen compound for use in the present invention is estratriene-3-ol.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The compositions of the present invention comprise one or more non-feminizing estrogens and a pharmaceutically acceptable vehicle. As used herein, the term "pharmaceutically acceptable vehicle" refers to any formulation which is acceptable, i.e., safe and provides the appropriate delivery for the desired route of administration, of an effective amount of one or more non-feminizing estrogens. The compositions of the present invention may be administered in a variety of different ways including systemically (e.g., oral administration, intramuscular injection, subcutaneous injection, intravenous injection, transdermal administration and transmucosal administration), topically and by intraocular injection, intraocular perfusion, periocular injection or retrobulbar (sub-tenon) injection.

The exact dosage of the non-feminizing estrogen(s) will vary, but will be determined by skilled clinicians in the art. Various factors affecting the dosage amount include the actual disease to be treated, the severity of condition, the health of the patient, the potency and specific efficacy of the non-feminizing estrogen, and so on. The determination of the appropriate dosage amount is well within the skills of the ordinary artisan. The amount dosed, however, will be in an effective amount to prevent, treat or ameliorate an ocular disease or disorder, e.g., those described herein; such an amount is referred herein as an "effective amount." In general, the daily dosage of non-feminizing estrogens will range between about 0.001 and 100 milligrams per kilogram body weight per day (mg/kg/day), and preferably between about 0.01 and 5.0 mg/kg/day.

The non-feminizing estrogens of the present invention may be contained in various types of ophthalmic compositions, in accordance with formulation techniques known to those skilled in the art. For example, the compounds may be included in solutions, suspensions and other dosage forms adapted for topical, intravitreal or intracameral use.

Aqueous compositions are generally preferred, based on ease of formulation and physiological compatibility. However, the non-feminizing estrogens of the present invention may also be readily incorporated into other types of compositions, such as suspensions and viscous or semi-viscous gels or other types of solid or semi-solid compositions for topical or retrobulbar injection. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Topical ophthalmic products are typically packaged in multi-dose form. Preservatives are thus required to prevent microbial contamination during use. Suitable preservatives include: benzalkonium chloride, chlorobutanol, methyl paraben, propyl paraben, phenylethyl alcohol, edetate disodium, sorbic acid, polyquaternium-1, or other agents known to those skilled in the art. Some of these preservatives, however, may be unsuitable for particular applications, (e.g., benzalkonium chloride may be unsuitable for intraocular injection). Such preservatives are typically employed at a level of from 0.001 to 1.0% weight/volume ("% w/v").

The topical dosage for topical administration of non-feminizing estrogens generally will range between about 1-2 two drops administered to the eye 1-4 times per day of a composition comprising 0.001 and 5% weight/volume ("w/v"), and preferably between 0.1 and 1% (w/v) of one or more non-feminizing estrogens. Solutions, suspensions, ointments, gels, jellies and other dosage forms adapted for topical administration are preferred. Additionally, non-feminizing estrogens may be delivered slowly, over time, to the afflicted tissue of the eye through the use of contact lenses. This regimen is generally performed by first soaking the lenses in a non-feminizing estrogen solution, and then applying the contact lenses to the eye for normal wear.

The compositions of the present invention are further illustrated in the following formulation examples, non-feminizing estrogens of the present invention are represented generically in the examples as "Non-feminizing estrogen."

Example 1

A topical ophthalmic composition useful for treating retinal vascular diseases:

| Ingredient | Concentration (% w/v) |
| --- | --- |
| Non-feminizing estrogen | 0.1 |
| Dibasic Sodium Phosphate | 0.2 |
| HPMC | 0.5 |
| Polysorbate 80 | 0.05 |
| Benzalkonium Chloride | 0.01 |
| Sodium Chloride | 0.75 |
| Edetate Disodium | 0.01 |
| NaOH/HCl | q.s., pH 7.4 |
| Purified Water | q.s. 100% |

Example 2

A sterile intraocular injection solution useful for treating retinal vascular diseases:

| Ingredient | Concentration (% w/v) |
| --- | --- |
| Non-feminizing estrogen | 0.05-5.0 |
| Cremophor EL ® | 10 |
| Tromethamine | 0.12 |
| Mannitol | 4.6 |
| Disodium EDTA | 0.1 |
| Hydrochloric acid or sodium hydroxide | q.s., pH to 7.4 |
| Water for injection | q.s. 100% |

Example 3

A tablet formulation suitable for oral administration, and useful for treating retinal vascular diseases:

| Ingredient | Amount per Tablet (mg) |
| --- | --- |
| Non-feminizing estrogen | 200 |
| Cornstarch | 50 |
| Lactose | 145 |
| Magnesium stearate | 5 |

Example 4

An systemic injectable solution useful for treating retinal vascular diseases:

| Ingredient | Amount |
| --- | --- |
| Non-feminizing estrogen | 200 mg |
| 0.4M KH2PO4 solution | 2 ml |
| 1 N KOH solution | q.s. to pH 7.0 |
| Water for injection | q.s. to 20 ml |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

United States Patents
U.S. Pat. No. 5,843,934
U.S. Pat. No. 5,877,169
U.S. Pat. No. 6,001,368
U.S. Pat. No. 6,197,833
Publications
Alkayed et al., "*Neuroprotective effects of female gonadal steroids in reproductively senescent female rats*", STROKE, vol 31, pp 161-168 (2000)
Allred et al., "*Soy diets containing varying amount of genistein stimulate growth of estrogen-dependent* (MCF-7) *tumors in a dose-dependent manner*", CANCER RES, vol 61, pp 5045-5050 (2001)
Chen et al., "*The effects of 17beta-estradiol on ischemia-induced neuronal damage in the gerbil hippocampus*", NEUROSCIENCE, vol 87, pp 817-822 (1998)
Controneo and Lamartiniere, "*Pharmacologic, but not dietary, genistein supports endometriosis in a rat model*", TOXICOL SCI, vol 61, pp 68-75 (2001)
Culmsee et al., "*Neuroprotection by estrogens in a mouse model of focal cerebral ischemia and in cultured neurons: evidence for a receptor-independent antioxidative mechanism*", J CEREB BLOOD FLOW METAB, vol 19, pp 1263-1269 (1999)
Dubal et al., "*Estradiol protects against ischemic injury*", J CEREB BLOOD FLOW METAB, vol 18, pp 1253-1258 (1998)
Green and Simpkins, "*Neuroprotective effects of estrogens: Potential mechanisms of action*", INT J DEV NEUROSCI, vol 18, pp 347-358 (2000)

Harris-Yitzhak M. et al., "*Estrogen-replacement therapy: Effects on retrobulbar hemodynamics*", AM J OPHTHALMOL, vol 129, pp 623-628 (2000)

Hawk et al., "*Testosterone increases and estradiol decreases middle cerebral artery occlusion lesion size in male rats*", BRAIN RES, vol 796, pp 296-298 (1998)

Hurn and Macrae, "*Estrogen as a neuroprotectant in stroke*", J CEREB BLOOD FLOW METAB, vol 20, pp 631-652 (2000)

Kondo et al, "*Estrogen alleviates cognitive dysfunction following transient brain ischemia in ovariectomized gerbils*", NEUROSCI LETT, vol 238, pp 45-48 (1997)

Maggiolini et al., "*Estrogen receptor alpha mediates the proliferative but not the cytotoxic dose-dependent effects of two major phytoestrogens on human breast cancer cells*", MOL PHARMACOL, vol 60, pp 595-602 (2001)

Nonaka et al., "*Administration of 17 beta-estradiol attenuates retinal ischemia-reperfusion injury in rats*", INVEST OPHTHALMOL VIS SCI vol 41, pp 2689-2696 (2000)

Pelligrino et al., "*Cerebral vasodialting capacity during forebrain ischemia: effects of chronic estrogen depletion and repletion and the role of neuronal nitric oxide synthase*", NEUROREPORT, vol. 9, pp 3285-3291 (1998)

Rusa et al., "*17 beta-estradiol reduces stroke injury in estrogen-deficient female animals*", STROKE, vol 30, pp 1665-1670 (1999)

Shi et al., "*Effects of 17 beta-estradiol on glucose transporter 1 expression and endothelial cell survival following focal ischemia in the rats*", EXP BRAIN RES, vol 117, pp 200-206 (1997)

Simpkins et al., "*Estrogens may reduce mortality and ischemic damage caused by middle cerebral artery occlusion in the female rat*", J NEUROSURG, vol 87, pp 724-730 (1997)

Toung et al., "*Estrogen-mediated neuroprotection after experimental stroke in male rats*", STROKE, vol 29, pp 1666-1670 (1998)

Wang et al., "*Estrogen provides neuroprotection in transient forebrain ischemia through perfusion-independent mechanisms in rats*", STROKE, vol 30, pp 630-637 (1999)

Yannuzzi et al., "*Risk factors for central retinal vein occlusion*", ARCH OPHTHALMOL, vol 114, pp 545-554 (1996)

Zhang et al., "*Effects of gender and estradiol treatment on focal brain ischemia*", BRAIN RES, vol 784, pp 321-324 (1998)

I claim:

1. A method for treating a retinal vascular disease selected from the group consisting of a retinal arterial obstructive disease, central retinal vein occlusion, and retinal branch vein occlusion, said method comprising administering to a patient in need thereof a therapeutically effective amount of a composition comprising at least one non-feminizing estrogen compound, wherein said non-feminizing estrogen compound is estratriene-3-ol.

2. The method of claim 1, wherein said retinal vascular disease is a retinal arterial obstructive disease.

3. The method of claim 2, wherein said retinal arterial obstructive disease is selected from the group consisting of central retinal artery obstruction, branch retinal artery obstruction, cilioretinal artery obstruction, ophthalmic artery obstruction, combined central retinal artery and vein obstruction, and cotton-wool spots.

* * * * *